United States Patent
Maschke

(10) Patent No.: US 7,192,188 B2
(45) Date of Patent: Mar. 20, 2007

(54) APPARATUS AND METHOD FOR CONDUCTING MEDICAL PROCEDURES ON MULTIPLE PATIENTS RESPECTIVELY AT DIFFERENT LOCATIONS

(75) Inventor: Michael Maschke, Lonnerstadt (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/888,617

(22) Filed: Jul. 9, 2004

(65) Prior Publication Data
US 2005/0031087 A1 Feb. 10, 2005

(30) Foreign Application Priority Data
Jul. 10, 2003 (DE) ................. 103 31 246

(51) Int. Cl.
*H05G 1/02* (2006.01)
*H05G 1/08* (2006.01)

(52) U.S. Cl. .............. 378/197; 378/114; 378/115; 378/196

(58) Field of Classification Search ............ 378/197, 378/20, 68, 208, 209, 114, 115, 116, 196, 378/205
See application file for complete search history.

(56) References Cited

U.S. PATENT DOCUMENTS

| 3,714,427 A | * | 1/1973 | Reiniger et al. | 378/25 |
| 5,048,070 A | * | 9/1991 | Maehama et al. | 378/197 |
| 5,288,977 A | * | 2/1994 | Amendolia et al. | 235/375 |
| 5,877,501 A | * | 3/1999 | Ivan et al. | 250/370.09 |

FOREIGN PATENT DOCUMENTS

| DE | 3732194 A1 | * | 4/1988 |
| DE | 199 41 237 | | 3/2001 |

\* cited by examiner

*Primary Examiner*—Edward J. Glick
*Assistant Examiner*—Chih-Cheng Glen Kao
(74) *Attorney, Agent, or Firm*—Schiff Hardin LLP

(57) ABSTRACT

In a method and an apparatus for conducting a medical procedure on a number of patients respectively disposed at a number of different locations, a component of a medical device for implementing the medical procedure is moved along a pre-assembled track that extends to each of the locations. When the component is moved to the intended location by the track, the medical procedure is implemented at that location with the component retained on the track.

13 Claims, 2 Drawing Sheets

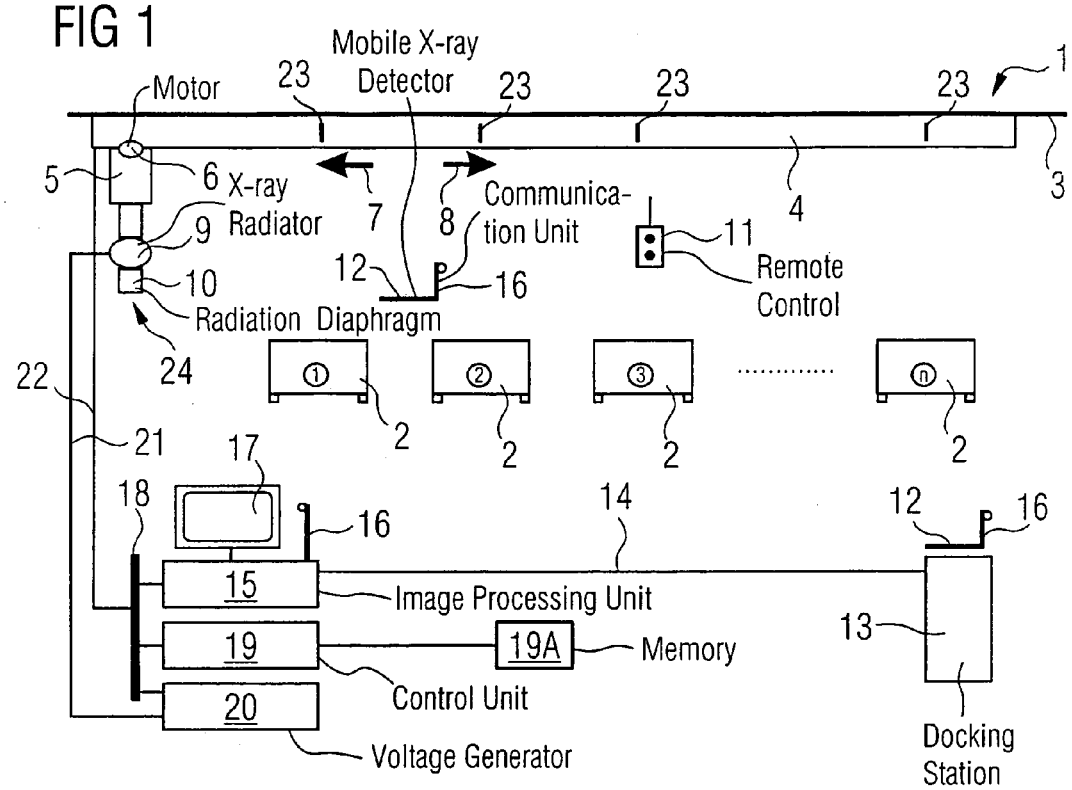
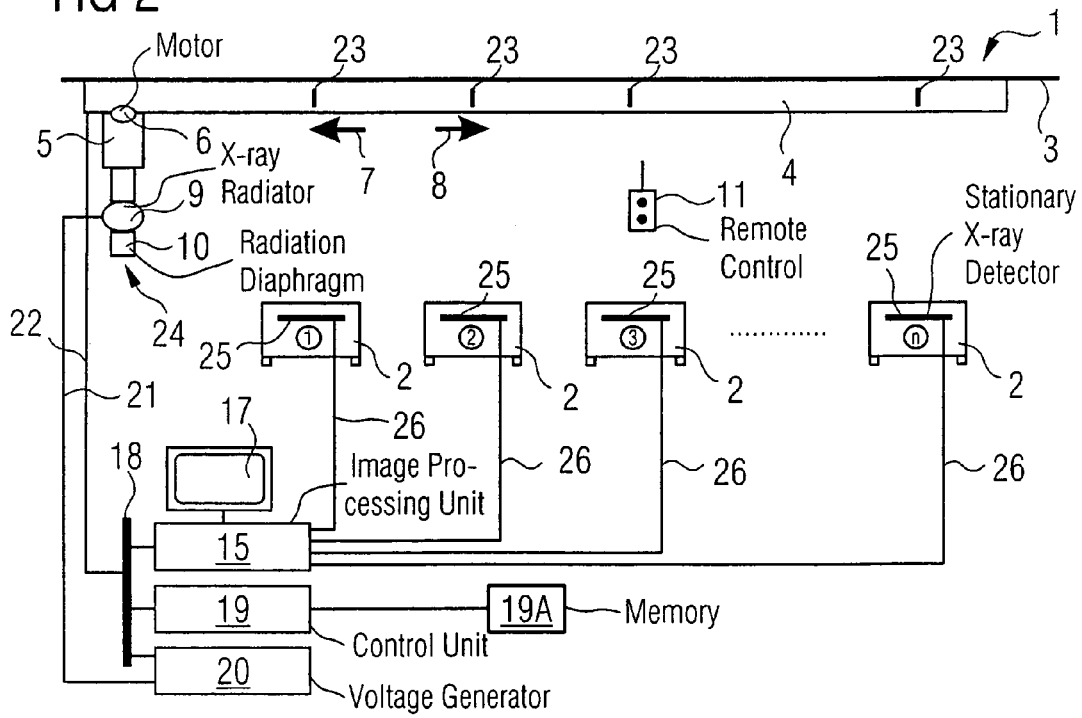

APPARATUS AND METHOD FOR CONDUCTING MEDICAL PROCEDURES ON MULTIPLE PATIENTS RESPECTIVELY AT DIFFERENT LOCATIONS

BACKGROUND OF THE INVENTION

1. Field of the Invention

The present invention concerns an apparatus to implement a medical procedure on a number of patients respectively located on various resting places with a transport apparatus with whose help a component of the apparatus necessary to implement the medical procedure can be transported to the various resting places of the patients.

The invention also concerns a method to implement a medical procedure on a number of patients respectively located at various resting places.

2. Description of the Prior Art

Apparatuses and methods of the above general type are known in the field of intensive care medicine. An example is known as the thorax overview exposure, which numbers among the most frequent imaging examinations in the field of medical technology. The thorax overview exposure normally is implemented daily on each patient in the intensive care unit in order, for example, to determine whether water is accumulating in the lungs or whether a lung inflammation is developing. To implement the x-ray exposure, a film cassette serving as an x-ray detector is placed under the patient. An x-ray apparatus with an x-ray radiator is subsequently moved by medical personnel to the bed of the patient to be examined.

A disadvantage of such known apparatuses and methods is that the x-ray apparatus weighing several hundred kg, must be moved by medical personnel by hand to the bed of the respective patient to be examined. Moreover, in spite of the high weight, the voltage generator capacity of such a mobile x-ray apparatus is limited. The limiting generator capacity leads to a limited radiation power, wherefore the quality of the x-ray exposures acquired with the mobile x-ray apparatus is normally poorer than the quality of the x-ray exposures acquired with a stationary x-ray apparatus. Moreover, that radiation load associated with the use of mobile x-ray apparatuses is high, because longer exposure times must be used to implement the x-ray exposure, due to the lower radiation power.

SUMMARY OF THE INVENTION

An object of the present invention is to provide an improved apparatus and an improved method of the above type to implement a medical procedure on a number of patients respectively located at various places.

This object is achieved by an apparatus and a method in accordance with the invention wherein a component of the medical apparatus for implementing the medical procedure is moved along a pre-assembled transport track, extending to a number of patient locations, to the location of that patient on whom the medical procedure is to be implemented.

The use of a pre-assembled transport track to move the component enables the component to be fashioned without consideration of its weight, allowing the medical procedure to be implemented in a shorter amount of time with better quality. The positioning of the component is also unproblematic since this is directed by the pre-assembled transport track.

In a preferred embodiment, the transport track extends above the patient locations. This is of advantage since generally a lot of space is available above the locations, such as patient beds, so that voluminous components also can be moved without the apparatuses located in proximity to the patient location having to be moved aside from the path of the components.

In a further preferred embodiment, the apparatus is equipped with a positioning device that allows it to align the component precisely to the location of the respective patient to be examined or to be treated. In particular in the implementation of imaging methods, this leads to a greater precision in the implementation composed to alignment by visual judgment, which regularly results in unusable exposures.

The component preferably is moved along the transport track with the aid of a motor. This significantly reduces physical stress on the medical personnel.

In a further preferred embodiment, the component is an x-ray radiator that can be moved above the patient locations, such as beds. The x-ray exposures are implemented respectively using mobile x-ray detectors that are brought to the location of the respective patient to be examined. By the transport of the x-ray radiator along a pre-assembled transport path, it is possible to fashion the x-ray radiator without consideration of its weight, so that the x-ray exposure can be implemented in a shorter amount of time with better quality and with lower radiation exposure for the patient.

In a further preferred embodiment, x-ray detectors that can be connected to data lines are integrated into the locations for the patients. The x-ray detectors can be read out via these data lines. The necessity of raising the patient before the x-ray exposure in order to, for example, place a film cassette under the patient thus is omitted. It is also no longer necessary to remove the film cassette in the same manner after the x-ray exposure.

DESCRIPTION OF THE DRAWINGS

FIG. 1 shows a first exemplary embodiment of an x-ray system in accordance with the invention with which x-ray exposures can be implemented on a number of bedridden patients.

FIG. 2 shows a modified embodiment of the x-ray system of FIG. 1.

DESCRIPTION OF THE PREFERRED EMBODIMENTS

Figure 3:
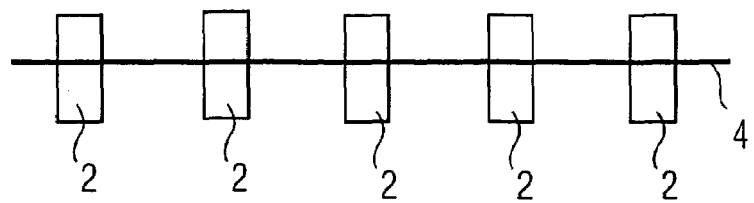
FIG. 3 schematically illustrates a view from above of the system of FIG. 1.

In FIG. 1, an x-ray system is shown with which x-ray images can be acquired of patients in respective patient beds 2. In FIG. 1, n patient beds 2 are located in the room of an intensive care unit. A ceiling rail 4 along which a radiator mount 5 can be moved with the aid of a motor 6 is mounted on a ceiling 3 of this room. The radiator mount 5 can be moved with the aid of the motor 6 both in a forward direction 7 and in a backward direction 8. An x-ray radiator 9 with a radiation-gating diaphragm 10 is attached to the radiator mount 5. The traveling motion of the radiator mount 5 along the ceiling rail 4 and the back-and-forth movement of the radiator mount 5 can be controlled with a remote control 11. Furthermore, it is also possible to adjust the diaphragm 10 and to trigger the irradiation by the x-ray radiator 9 with the remote control 11.

The x-ray images are acquired by a mobile x-ray detector 12 that can be inserted into the patient bed 2 of the patient to be examined, for example, a solid-state detector based on amorphous silicon. The mobile x-ray detector 12 can be equipped with an accumulator (rechargeable battery) power supply (not shown) as well as with components (likewise not shown) that serve for the pre-processing and buffering of the images and the acquisition of patient information data. In particular, data for identification of the patient to be examined can be stored in the mobile x-ray detector 12.

After the acquisition of the x-ray image, the mobile x-ray detector 12 is brought to a charging station in which an electrical contact between the mobile x-ray detector 12 and the charging station is established with a mechanical contacting device 12. The mobile x-ray detector 12 subsequently can be charged. Any data stored in the mobile x-ray detector 12 also can be downloaded. For this purpose, the docking station 13 is connected via a data line 14 with an image-processing unit 15.

In addition to this, it is possible (as shown in FIG. 1) to provide the mobile x-ray detector 12 and the image-processing unit 15 with communication units 16 that serve for wireless communication between the mobile x-ray detector 12 and the image-processing unit 15. The communication units 16 can operate on the basis of Bluetooth technology or communicate by means of a WLAN. Both techniques are known to those skilled in the art and are as such not the subject matter of the present application.

The image-processing unit 15 is connected with a display 17 on which the generated x-ray image can be shown. The image-processing unit 15 also is connected via system bus lines 18 to a control unit 19. A generator 20 which supplies the x-ray radiator 9 with the necessary high voltage via supply cables 21 is also connected with the system bus lines 18.

A data line 22 to which position sensors 23 are connected in the region of the ceiling rail 4 is also attached to the system bus lines 18.

The x-ray system can be operated as follows:

Using the motor 6, the radiator mount 5 can be driven from its standby position 24 to each of the patient beds 2. The motor 6 automatically stops when the desired position over the patient bed 2 with the patient to be examined is reached. The radiator mount 5 subsequently is adjusted with regard to height with the aid of the remote control 11 and is pivoted until it has achieved the position necessary for acquisition of the x-ray image.

The mobile x-ray system 12 at the docking station 13, having had its accumulators charged in the docking station 13, is subsequently brought to the patient bed 2 of the patient to be examined and is placed under the patient.

Each patient is unambiguously identified by the position sensors 23 over the patient beds 2. Information regarding the patient and pre-adjustments (presets) for acquisition of x-ray images can be retrieved by the control unit 19 from a memory 19A. The radiator mount 5, the x-ray radiator 9 and in particular the depth diaphragms 10 are set corresponding to this information. The medical personnel needs this information only for checking, and can trigger the x-ray exposure when the mobile x-ray detector detects, with the aid of its communication unit 16 and the position sensor 23, that it is at the correct patient bed 2 and that the x-ray exposure is enabled.

After the implementation of the x-ray exposure, the digital x-ray image is sent to the image-processing unit 15 via the communication unit 16 and there revised with the aid of an image-processing program. The revised image is shown on the display 17 and can immediately be checked by the medical personnel, which is a significant advantage for patients in the intensive care unit.

The x-ray radiator 9 is subsequently moved to the next patient bed 2 and the mobile x-ray detector 12 is placed under the next patient.

After all patients have been examined, the mobile x-ray detector 12 is brought back to the docking station 13 in order to charge the accumulator thereof. Moreover, the mobile x-ray detector 12 is synchronized with the image-processing unit 15 and prepared for the next x-ray exposures.

In a modified embodiment, the images of all patients of the intensive care unit are cached in the mobile x-ray detector 12. In this embodiment, the x-ray images are sent to the image-processing unit 15 only when the x-ray acquisitions have been implemented on all patients.

The x-ray system specified herein offers a series of advantages:

Because the association of the acquired x-ray images with a specific patient bed 2 is monitored by the x-ray system 1, the x-ray exposure can be unambiguously associated with a patient. Confusion of x-ray exposures as often occurs in known systems is therefore nearly impossible.

Since the x-ray radiator 9 is attached to the ceiling rail 4 via the radiator tripod 5, the x-ray radiator 9 can thus be designed such that sufficient radiation capacity is available for x-ray images of high quality. The x-ray radiator 9 hanging from the ceiling can be moved into the respective working position over the patient beds 2 without this movement impeding other medical apparatuses such as infusion racks, respiration apparatuses or patient monitors.

In FIG. 2, a further modified x-ray system 1 is shown in which the patient bed 2 is equipped with a stationary x-ray detector 25. The stationary x-ray detectors 25 are connected via data lines 26 with the image-processing unit 15.

In this embodiment of the x-ray system 1, only the x-ray radiator 9 needs to be moved into the respective working position. Transport of the mobile x-ray detector 12 is omitted. The patients therefore do not need to be raised in order to place the x-ray detector in the patient bed 2. The stress due to the raising of the patients is thereby omitted.

In a further modified embodiment, a mobile x-ray detector is used, but in this embodiment the data communication between mobile detector and the image processing system 15 is accomplished with cables. For this, a connection socket that is connected with the image-processing unit 15 via a fixed, laid cable is provided next to each patient bed 2.

An advantage of this embodiment is that the energy required by the mobile detector can also be supplied via the cable connection, and an accumulator with low storage capacity is sufficient for the mobile detector.

In addition, various embodiments of the ceiling rail 4 are also possible. FIG. 3 shows a view of the x-ray system 4 from above. In FIG. 3, a ceiling rail 4 crossing a number of patient beds 2 and extending in a straight line is clearly visible.

Figure 4:
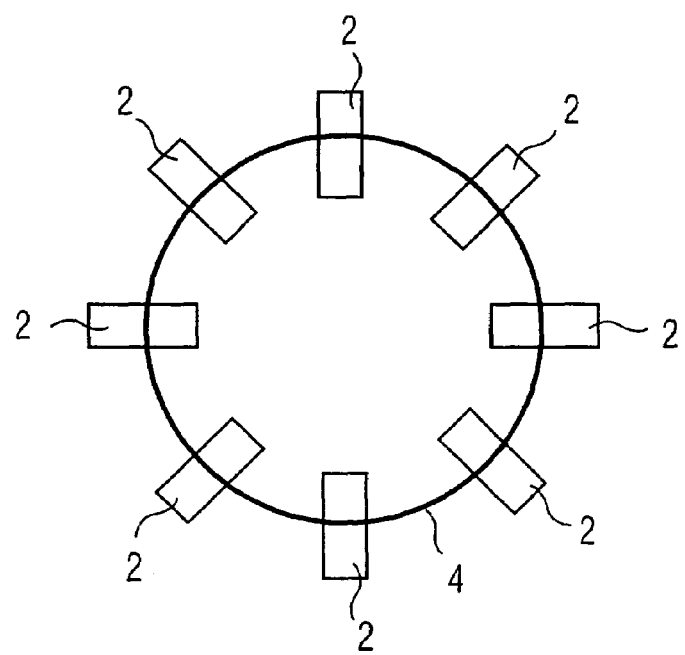
FIG. 4 schematically illustrates a view from above of an x-ray system in accordance with the invention with a modified design of the ceiling rail.

In the embodiment of FIG. 4 the detector rail 4 likewise crosses a number of patient beds but runs along a circular path.

Figure 5:
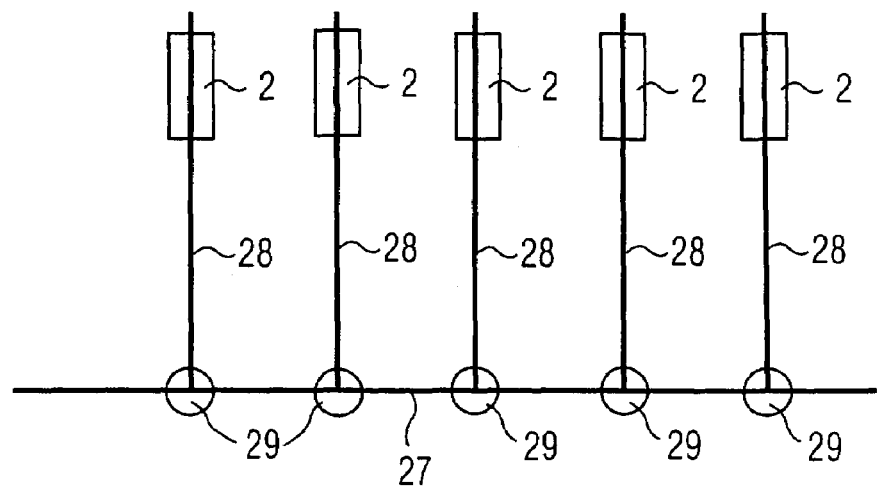
FIG. 5 schematically illustrates a view from above of a further modified x-ray system in accordance with the invention that has a main rail from which a series of adjacent rails branch.

The ceiling rail in FIG. 5 has a main rail 27 that is, for example, arranged in a corridor. Adjacent rails 28 branch from the main rail 27, the adjacent rails 28 respectively leading to the patient beds 2 disposed in separate rooms and connected with the main rail 27 via switches 29.

The concept described herein is not limited to x-ray apparatuses. Other medical apparatuses can be mounted on a ceiling rail and be moved across the patient beds 2 to the respective patients to be examined or treated. In addition to x-ray apparatuses, other radiation sources or detectors for imaging methods can be considered. Therapy apparatuses also can be moved in this way to the respective patient to be treated.

It should also be noted that guidance and transport of the apparatuses via a rail laid on the floor can be employed.

Although modifications and changes may be suggested by those skilled in the art, it is the intention of the inventor to embody within the patent warranted hereon all changes and modifications as reasonably and properly come within the scope of his contribution to the art.

I claim as my invention:

1. An apparatus for conducting a medical procedure on a plurality of patients respectively disposed at a plurality of different locations, comprising:
    a medical device having a component for implementing a medical procedure;
    a transport device connected to said component for moving said component to the respective locations;
    a pre-assembled transport track engaging said transport device and proceeding to each of said plurality of different locations, said transport device being movable along said transport track to each of said plurality of different locations;
    a memory containing stored information regarding each patient in said plurality of patients, and stored sets of parameters for operating said medical device to implement a medical procedure at each location in said plurality of different locations;
    a positioning device that aligns said component to one of said locations in said plurality of locations and that unambiguously identifies said one of said locations; and
    a control unit that interacts with said positioning device and said memory to identify the patient at said one of said locations and to cause said medical device to implement a medical procedure using the stored set of parameters for said one of said locations.

2. An apparatus as claimed in claim 1 wherein said transport track is adapted to cross over each of said plurality of different locations.

3. An apparatus as claimed in claim 1 wherein said transport track comprises a ceiling track adapted for mounting to a ceiling of a room containing said plurality of different locations.

4. An apparatus as claimed in claim 1 wherein said positioning device comprises a plurality of position sensors disposed along said transport track respectively at said plurality of different positions, said positioning device interacting with said plurality of position sensors, one at a time, to unambiguously identify the patient at one of said plurality of different positions.

5. An apparatus as claimed in claim 1 wherein said component comprises an x-ray radiator.

6. An apparatus as claimed in claim 5 wherein said medical device further comprises a movable x-ray detector adapted for insertion at the respective different locations in said plurality of locations in a position beneath a patient at that location.

7. An apparatus as claimed in claim 6 wherein said movable x-ray detector comprises a rechargeable power supply, and wherein said apparatus comprises a docking station adapted to temporarily receive said movable x-ray detector for recharging said power supply thereof.

8. An apparatus as claimed in claim 7 wherein said movable x-ray detector comprises a communication unit for downloading x-ray image data detected by said movable x-ray detector, and wherein said docking station comprises a data receptacle for receiving said x-ray image data when said movable x-ray detector is in said docking station.

9. An apparatus as claimed in claim 6 wherein said movable x-ray detector comprises a wireless communication unit for downloading x-ray image data detected by the movable x-ray detector wirelessly to a remote receiver.

10. An apparatus as claimed in claim 5 comprising a plurality of stationary x-ray detectors respectively disposed at said plurality of different locations.

11. A method for conducting a medical procedure on a plurality of patients respectively located at a plurality of different locations, comprising the steps of:
    providing a pre-assembled transport track extending to each of said plurality of different locations;
    non-manually moving a component of a medical device, for implementing a medical procedure, along said transport track to each of said locations and conducting said medical procedure at the respective locations using said component on said transport track;
    automatically electronically aligning said component at one of said locations in said plurality of locations;
    automatically unambiguously identifying a patient at said one of said locations;
    from memory, automatically retrieving a stored set of parameters for said medical device for implementing a medical procedure at said one of said locations; and
    automatically electronically controlling said medical device to implement said medical procedure at said one of said locations using said component on said track and using the stored set of parameters from said memory for implementing the medical procedure at said one of said locations.

12. A method as claimed in claim 11 comprising employing an x-ray radiator as said component and obtaining an x-ray image of a patient at each location as said medical procedure.

13. A method as claimed in claim 11 comprising, at each location in said plurality of different locations, automatically electronically detecting patient information at that location to identify the patient at that location.

* * * * *